May 15, 1973 L. W. LENZ Plant Pat. 3,332
MAHONIA SHRUB
Filed June 4, 1971
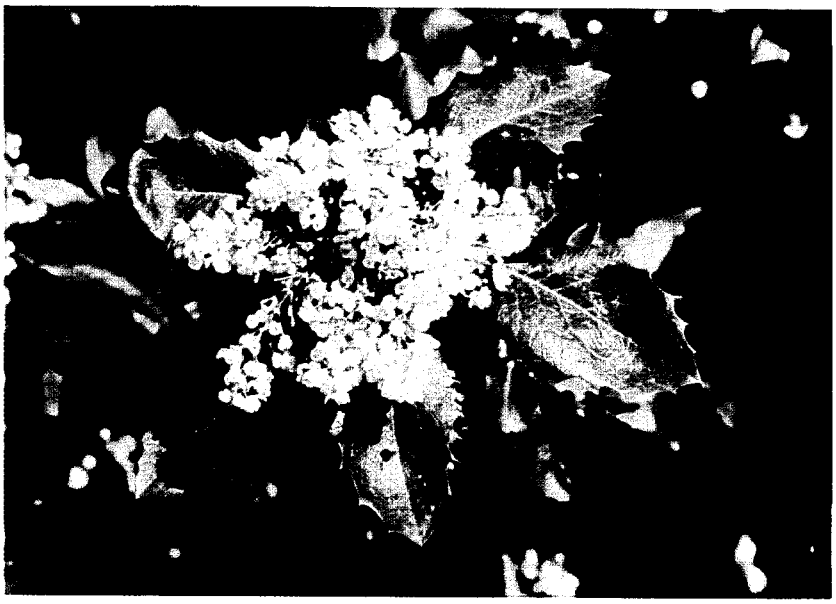
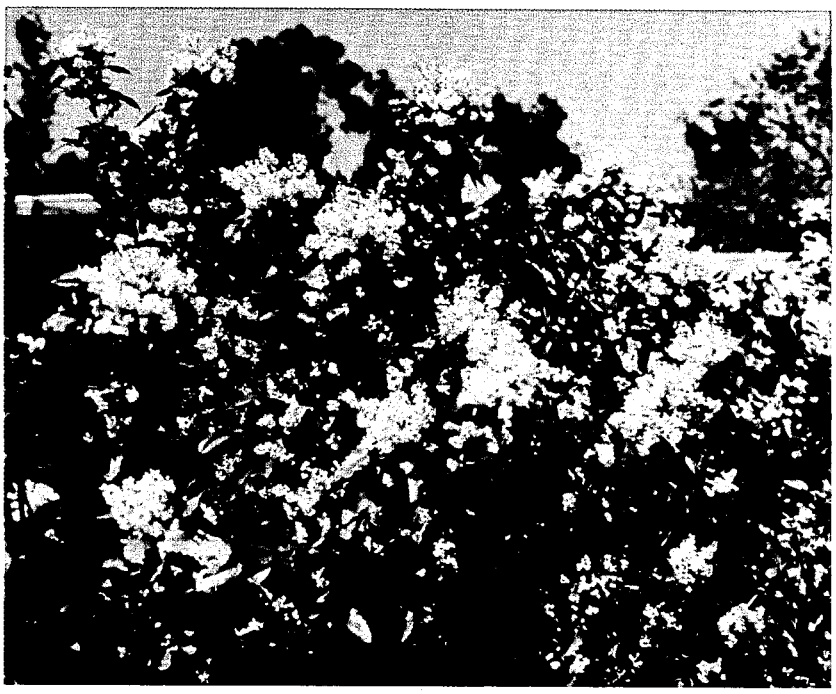
INVENTOR.
LEE W. LENZ,
By Edmond F. Shanahan
ATTORNEY.

United States Patent Office

Plant Pat. 3,332
Patented May 15, 1973

3,332
MAHONIA SHRUB

Lee W. Lenz, Claremont, Calif., assignor to Rancho Santa Ana Botanic Garden

Filed June 4, 1971, Ser. No. 149,894
Int. Cl. A01h 5/00
U.S. Cl. Plt.—54 1 Claim The present invention relates to a new and distinct hybrid of the genus Mahonia. In this patent application, the Mahonia shrub is treated as distinct from the genus Berberis, following the classification of Rehder, "Manual of Cultivated Trees and Shrubs," second edition, 1947, and Bailey, "Standard Cyclopedia of Horticulture," 1925. Under the classification here used, Mahonia is recognized as separate and distinct from Berberis, with Mahonia characterized as having pinnate leaves and unarmed branches. (Some botanical authors submerge Mahonia into the genus Berberis, e.g., Munz and Keck, "A California Flora," 1959.)

The Mahonia shrub of the invention is characterized as to novelty by flower and fruit characteristics different from either its pollen parent or its seed parent. The invention is characterized by the very large zice of the terminal inflorescence, with many branches bearing numerous flowers; and by the large number of lateral inflorescence produced along the stems. Following the blooming season, the flowers are replaced by numerous and drooping racemes of globose, purplish-blue fruit with a bloom. The shrub of the invention is also characterized and distinguished from its parents by its vigorous erect-spreading branches, which attain a height of two and one-half meters, and by the shrub's dark glossy green leaves, which combine a color and physical structure not found in combination with either parent alone.

The plant originated by chance hybridization between *Mahonia amplectans* and a hybrid plant of the presumed parentage of *Mahonia aquifolium* and *M. piperiana*. From a population of plants grown from seed collected from *M. amplectans* I selected this plant as being superior to any other plant in the population and this single plant has ben asexually propagated by cuttings, all showing the same characteristics. The novel Mahonia will not reproduce true from seed. Like its parents, it is resistant to stem rust of wheat as tested by the United States Department of Agriculture Rust Laboratory, St. Paul, Minn., and has been cleared by them for interstate shipment.

This hybrid Mahonia combines characteristics of *M. amplectans, M. equifolium and M. piperiana,* in some characters more closely resembling one species than another, in other characters it is intermediate between the parental species and in still other characteristics (date of blooming) it differs from all three species. Of the three species mentioned it most nearly resembles *M. amplectans* from which it differs in having a greater number of racemes of larger flowers, in having glossy green leaves rather than gray-glaucous leaves, in having fewer leaflets on each leaf and in having globose fruits rather than ovoid to elliptical fruits. It also blooms 8–10 days earlier than *M. amplectans* and the total length of bloom is longer than *M. amplectans*.

In the drawings (color photographs):

FIG. 1 is a picture of a five-year-old shrub, showing the characteristic appearance of the new variety; and FIG. 2 is a picture of the flowers of the new variety.

A detail description of the new variety follows and to facilitate identification of the important colors, the color terminology adopted by the Royal Horticulture Society Color Chart (1966 Ed.) System 189A has been followed.

DESCRIPTION OF THE PLANT

Parentage: Chance seedling, resulting from open pollination. Seed parent *Mahonia amplectans,* presumed pollen parent a hybrid between *Mahonia aquifolium* × *M. piperiana.*

*Growth*

Growth: The plant is of vigorous growth forming an erect-spreading shrub to about 2.5 m. high with multiple branches from the base, it does not have a central leader or trunk. The plant shown in the accompanying color print figures is five (5) years old and has a height of 2 meters.

Branches: New growth is at first light shiny green, later changing to dark shining green. Branches are erect-spreading.

Growth habit: Much branched from the base. No trunk is developed.

*Foliage*

Foliage: The foliage is thick and leathery with good substance. Mature leaves are yellow-green (RHS colour chart (147–A), glaucous below. The leaves on *Mahonia amplectans,* the seed parent, are grey-green (RHC 189–A) on the upper side and those of the presumed pollen parent are green (RHS 137–A).

Shape: The leaves of the invention are composed of 5–7 somewhat crowded to uncrowded, ovate to ovate-lanceolate leaflets each 2–6.5 cm. long and 1.3–5 cm. wide, truncate, broadly tapered to broadly oblique, with 12–18 spinules. The leaves of the seed parent are composed of 7–9 crowded, short and broad, rounded leaflets, 2–5.5 cm. long and 1.5–3.5 cm. wide, truncate to cordate to oblique at the base, with 16–19 spines. The leaves of the presumed pollen parent are composed of 5–7 leaflets, not crowded, lanceolate, 2–9 cm. long, 1.3–3 cm. wide, with 15–18 spinules.

*Flowers*

Flowers: Flowers typical of the genus, perfect; sepals 6, in 2 series, petal-like, falling early, subtended by 3 bractlets. Petals 6, in 2 series, with a pair of glands near the base; stamens 6, opposite the petals; ovary superior, one-celled, consisting of 1 carpel, stigma sessile. Fruit a few-seeded berry. The flowers of this invention have outer sepals which are about 4 mm. long, those of the seed parent are about 2.5–3 mm. long and those of the pollen parent are about 4.5 mm. long. The inner sepals are about 7–8 mm. long, of the seed parent 5.5–6 mm. long and the pollen parent about 8–9 mm. long. Both inner and outer sepals are yellow (RHS yellow group 9–A) and both the invention and the parents have the same color. The petals of the invention are about 5 mm. long, those of the seed parent about 4.5 mm. long and those of the pollen parent are about 6 mm. long. The color is yellow (RHS yellow group 6–A) and the invention and the parents are alike in color. The bracts of the invention are about 2–2.5 mm., margin broader, scariose, mildly erose, tip acute-acuminate, occ. slightly suggesting 2 lobes or shoulders. The bracts on the seed parent are about 2 mm., margin thin, scariose, entire-rounded or obtuse truncate. Those of the pollen parent are about 3 mm. margin scariose, somewhat erose or irregularly serrulate, acuminate and often with 2 acute lobes or shoulders.

*Fruit*

Fruit: The fruits of the invention are about 8–11 mm., mostly globose, purplish-blue with bloom. Those of the seed parent are about 10–11 mm. long, ovoid, ovoid-elliptic to elliptic, dark purplish with glaucous bloom. Those of the pollen parent are about 9–10 mm., ellipsoid-ovid, bluish purple with bloom.

Fruiting racemes: Those of the invention are 7–10 cm. long, very many, spreading-drooping, those of the seed parent are 7–19 cm. long, many, somewhat drooping or merely spreading, few weakly ascending. Those of the pollen parent are 2–2.5 cm. long, few, and stiff.

*Date of bloom*

Normal blooming period in southern California is February and March and the invention blooms about 8–10 days earlier than either parent and it remains for a longer period than either parent.

I claim:

1. A new and distinct hybrid of the shrub genus Mahonia, substantially as shown and described, characterized by a combination of features not found combined in previously known members of the genus, these features being the shape and profusion of the flowers, physical characteristics of the branches, the shape and peculiar color of the fruit, and the combination of large size and dark green leaves.

No references cited.

ROBERT E. BAGWILL, Primary Examiner